United States Patent [19]

Zudkevitch et al.

[11] 4,213,832

[45] Jul. 22, 1980

[54] DISTILLATION FOR SEPARATING DIALKYLKETONES FROM LOWER CHLOROHYDROCARBONS

[75] Inventors: David Zudkevitch, Dover; Nirmal K. Khanna, Scotch Plains; Robert F. Raczynski, Montague, all of N.J.

[73] Assignee: Allied Chemical Corporation, Morris Township, Morris County, N.J.

[21] Appl. No.: 917,608

[22] Filed: Jun. 21, 1978

[51] Int. Cl.² .................. B01D 3/38; C07C 45/24
[52] U.S. Cl. ........................ 203/95; 203/96; 568/410; 568/411
[58] Field of Search .............. 260/593 P; 203/96, 97, 203/92, 93, 76, 79, 83, 85, 50, 51

[56] References Cited

U.S. PATENT DOCUMENTS

| | | | |
|---|---|---|---|
| 2,662,848 | 12/1953 | Emerson et al. | 260/593 P |
| 3,198,837 | 8/1965 | Smidt et al. | 260/593 P |
| 3,276,973 | 10/1966 | Burmaster et al. | 260/593 P |
| 3,330,741 | 7/1967 | Theilig et al. | 260/593 P |
| 3,547,783 | 12/1970 | Yamaguchi et al. | 260/593 P |
| 3,686,078 | 8/1972 | Hauptmann et al. | 260/593 P |

OTHER PUBLICATIONS

Iino et al., "Removal of Small Amounts of Methylene Chloride in Acetone by Extr. Dist. Empl. Salts as Sep. Ags. Journal of Chemical Engineering of Japan, 4, No. 1, 1971 (p. 22).

Primary Examiner—Wilbur L. Bascomb, Jr.

[57] ABSTRACT

A process for separating the constituents of azeotropic mixtures of acetone and other lower ketones from lower halogenated hydrocarbons. Water is added to the azeotropic mixture of acetone and the lower halogenated hydrocarbon for breaking up of the azeotrope, and the halogenated halohydrocarbon is distilled off.

12 Claims, 1 Drawing Figure

SEPARATION OF ACETONE FROM DICHLOROMETHANE
BY EXTRACTIVE DISTILLATION

SEPARATION OF ACETONE FROM DICHLOROMETHANE
BY EXTRACTIVE DISTILLATION

DISTILLATION FOR SEPARATING DIALKYLKETONES FROM LOWER CHLOROHYDROCARBONS

FIELD OF THE INVENTION

This invention relates to a process for separating azeotropic mixtures of lower ketones and lower halogenated compounds.

BACKGROUND OF THE INVENTION

Acetone and other lower ketones form azeotropic mixtures with a number of lower halogenated compounds. Such azeotropes prevent effective separation of mixtures of such ketones and halogenated compound solvents by distillation. Ketones and halogenated compounds are encountered as result of or as solvents in chemical processes as mixtures in fiber production and recovery of the separate constituents of such mixtures is of commercial importance.

It is an object of the present invention to provide a method for separating acetone from certain lower halogenated compounds.

It is another object of the present invention to provide a method for separating dichloromethane from acetone.

SUMMARY OF THE INVENTION

A method is provided for separating dialkyl ketones having three to five carbon atoms such as acetone and methylethyl ketone, from their mixtures with certain halogenated compounds including lower halohydrocarbons and halo ethers, which form azeotropes with such ketones. In accordance with the present invention, this is accomplished by subjecting such mixtures to distillation in the presence of water. To that end the mixture of ketone and halogenated compound may be combined with water and the resultant mixture is subjected to distillation to obtain the halogenated compound essentially free of the ketone in the overhead product.

DETAILED DESCRIPTION OF THE INVENTION

Figure 1:
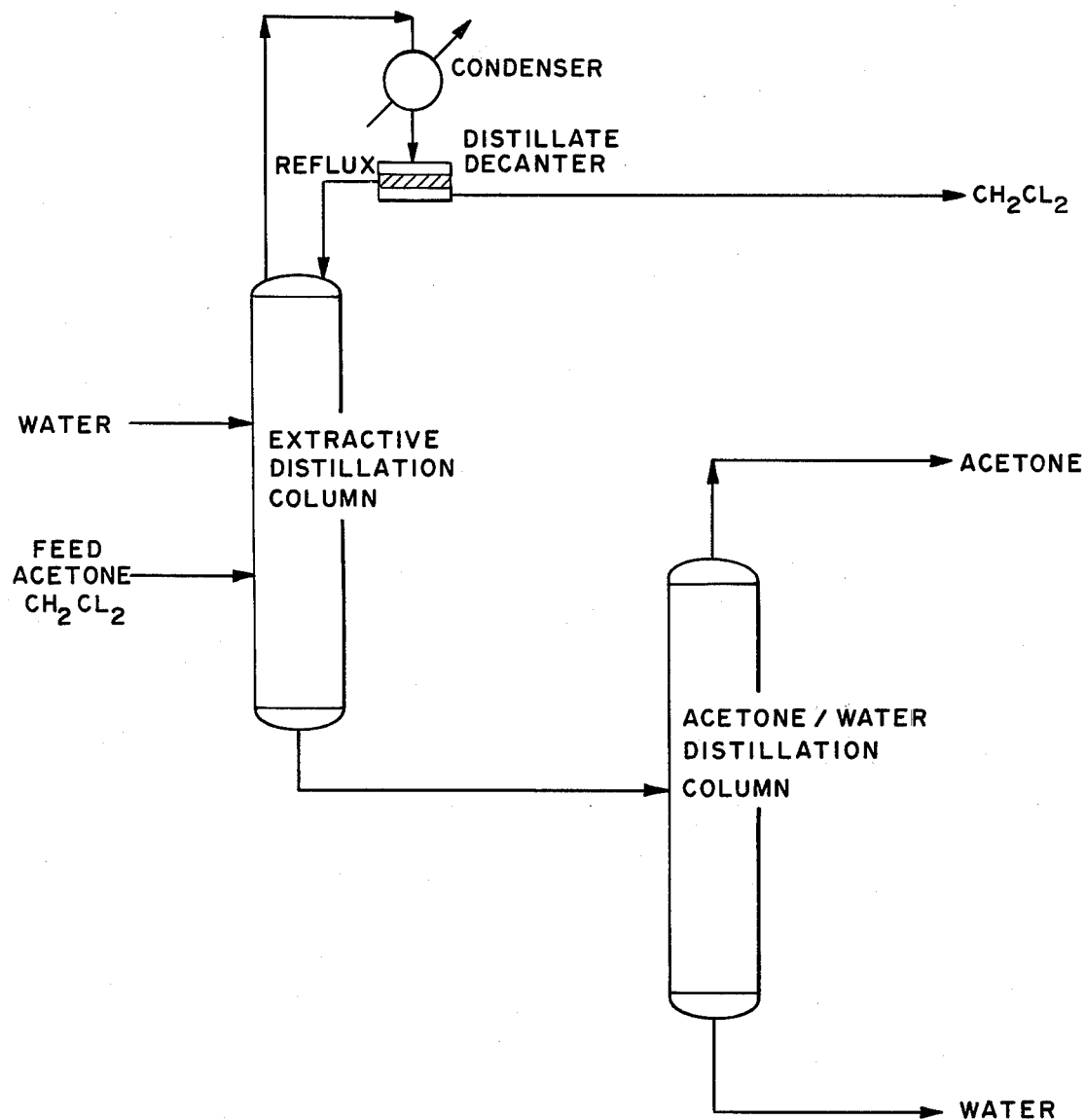
FIG. 1 shows a schematic diagram for separating acetone from dichloromethane by extractive distillation.

The present invention provides a method of separating lower dialkyl ketones from certain halogenated hydrocarbons and halogenated ethers where separation cannot be achieved by simple fractional distillation because of azeotrope or vapor liquid equilibrium pinch formation.

According to the present invention, lower halogenated compounds are removed from a mixture containing the ketone and one or more of certain halogenated hydrocarbons and/or halogenated ethers which form azeotropic mixtures with the ketone, by distilling such mixtures in the presence of water, as by adding water to the mixture and distilling it, to obtain the halogenated compound as essentially ketone free overhead product.

It has been found that water breaks azeotropes of the ketone and the halogenated compound. The lower ketones from which certain halogenated compounds can be separated in accordance with the invention process have the formulas $CH_3 CO CH_3$; $CH_3 CH_2 CO CH_3$; $(CH_3CH_2)_2CO$, $CH_3 CH_2 CH_2 CO CH_3$ and $(CH_3)_2 CH CO CH_3$.

Preferred ketones are acetone and methyl ethyl ketone, acetone being most preferred.

The halogen in the halogenated compounds can be chlorine and bromine with chlorine compounds preferred.

Halogenated compounds suitable in the separation process are the dihalogenated alkanes having two carbon atoms less than the ketone; monohalogenated alkanes with straight or branched carbon chains having the same number of carbon atoms as the ketone and not more than four carbon atoms if the halogen is bromine; monohalogenated monounsaturated hydrocarbons having the same number carbon atoms as the ketone; and monohalogenated dialkyl ethers having one carbon atom less than the ketone and mixtures thereof. Preferably the boiling point of the halogenated compound and of the ketone are below 100° C., more preferred under 80° C. and most preferred under 70° C.

Exemplary dihalogenated alkanes include 1,1-chloromethane, 1,1-chlorobromomethane, 1,1-dichloroethane. 1,1-dichloromethane is a preferred dihalogenated alkane.

Exemplary monohalogenated alkanes include 1-chloropropane, 2-chloro-2-methylpropane, 2-bromopropane, 2-chlorobutane, 1-chloro-2-methylpropane, 1-bromopropane, 1-chlorobutane, 2-chloropentane.

Preferred monohalogenated alkane are 1-chloropropane, 2-chloro-2-methylpropane, and 2-bromopropane.

Exemplary monohalogenated monounsaturated hydrocarbons include 3-chloropropane, 3-bromopropane, 4-chlorobutene-1. Exemplary monohalogenated dialkyl ethers include chloromethylmethyl ether and chloromethylethyl ether.

Exemplary halogenated compounds which form azeotropes with acetone (Boiling Point 56.15° C.) include 1,1-dichloromethane (B.P. 57.3° C., B.P. of azeotrope 57.55); chloromethyl methylether (B.P. 59.5° C., B.P. of azeotrope 55.9); 3-chloropropene (B.P. 45.15° C., B.P. of azeotrope 44.6° C.); 1-chloropropane (B.P. 46.65° C., B.P. of azeotrope 45.8° C.); 2-chloro-2-methylpropane (B.P. 50.8° C., B.P. of azeotrope 49.2° C.); 2-bromopropane (B.P. 59.4° C., B.P. of azeotrope 54.12° C.); 2-chlorobutane (B.P. 68.5° C., B.P. of azeotrope 55.75° C.); 1-chloro-2-methyl propane (B.P. 68.85° C., B.P. of azeotrope 55.75° C.); 1-bromopropane (B.P. 71° C., B.P. of azeotrope 56.18° C.); and 3-bromopropene (B.P. 70.5° C., B.P. of azeotrope 56.05° C.). Methyl ethyl ketone (B.P. 79.6° C.) forms an azeotrope with 1-chlorobutane (B.P. 78.5° C., B.P. of azeotrope 77° C.)

In an ideal solution the partial pressure, $\overline{P}_i$ of each component i above the solution is proportional to its concentration in the liquid phase. In nonideal solution it is not proportional to the concentration in the liquid phase and the deviation may be expressed as a correction factor activity coefficient g, which reduces to unity for ideal mixtures $$\overline{P}_i = X_i P_i^o g_i$$

where $\overline{P}_i$ = partial pressure of the component i $x_i$ = concentration of the component in the liquid solution $P_i^o$ = vapor pressure of pure component i; and $g_i$ = correction factor called the activity coefficient of component i.

The activity coefficient g varies with temperature and concentration. In an ideal mixture of two components, such as that of members of a homologous series the activity coefficients of both components of all concentrations equal unity. An azeotrope represents a specific case of a nonideal mixture.

The activity coefficient of any compound depends to an appreciable degree on the nature of the other compound or compounds in the solution and is usually different for each constituent of a solution. If in a system under low pressure, the ratio of the activity coefficients of the two components of a binary mixture at any concentration is equal to the inverse ratio of their respective vapor pressures at the given temperature, the vapor will have the same composition as the liquid. This particular mixture is known as an azeotrope and is characterized by a boiling point either lower or higher than either of the components. The boiling point will be lower, giving a minimum boiling mixture, when the mixture shows positive deviations from ideal mixing behavior or Raoult's law, which is the limiting definition of an ideal system under low pressure, and higher, giving a maximum boiling mixture, when the mixture shows negative deviations.

Azeotropes of the compounds to be separated can be of two types:
1. Those having a minimum boiling azeotrope; and
2. Those having a maximum boiling point azeotrope.

In the first case the bubble point and dew point curve of the isobaric temperature composition diagram have a minimum for the azeotropic temperature, and in the second case that curve shows a maximum.

In addition, a pinch in the vapor liquid equilibrium diagram whereby the composition difference diminishes and practically disapears is technically defined as a tangential azeotrope.

For example, at atmospheric pressure the acetone-1,1-dichloroethane system is of the maximum boiling type azeotrope. The azeotropes of mixtures of acetone with chloromethyl methylether, 3-chloropropene, 1-chloropropane 2-chloro-2 methyl propane are of the minimum type. For purposes of the present invention the type of the azeotrope involved is not critical.

When the azeotropic mixture consists of only a single liquid phase, it cannot be separated by ordinary fractional distillation.

The activity coefficients of two components of a solution containing a third component are generally different, in magnitude from their values in mixtures without a third component and if a distillation column can be operated to maintain a desired profile of the proper concentration of this third component in the column, then it can be possible to separate components which could not be separated in the absence of the third component due to the formation of an azeotrope or the tendency for a pinch in the vapor liquid equilibrium relationship. In such cases the relative volatility between the two components approaches unity.

A third component that does not form an azeotrope with either of the two original components will have a different effect on two dissimilar components and may therefore be used to separate them.

The third component can be selected that its mixture characteristics, quantitatively described by magnitude of the activity coefficients as they vary with composition, are such that they either change the relative volatility between the original two compounds or the temperature and pressure combination of the system to enable separation by either distillation, absorption, extraction or stripping.

When the third component is less volatile than both original components and its mixture characteristics are such that it does not form an azeotrope with either component but enhances the volatility of one component with relation to the other, the distillation is called extractive distillation.

Extractive distillation is preferably a continuous process and batch operation is less desirable since it requires continuous introduction of fresh solvent. It is desired that in extractive distillation the third component or solvent is much higher boiling and easily separated from the components of the original solution. As in all separation processes in order to maintain the desired concentration in the column, the third component is introduced at a point in the column where its usefulness is maximum. The third component is often introduced at the top section and is allowed to run down the column. By allowing sufficient trays above the solvent inlet to fractionate all of the solvent from overhead vapors, a substantially pure overhead product can be obtained. The solvent is removed from the bottom of the column with the other component. When employing a solvent which does not form azeotropes with either original component, the solvent is later separated from the other component by fractional distillation or other means as decantation, extraction or azeotropic distillation.

When the dissimilarity between one of the original components and the third component is such that these compounds do not completely mix when in the liquid state, thus forming two liquid phases and form a minimum boiling point heteroazeotrope whereby a vapor mixture can be at equilibrium with, or condense to form, two separate phases each containing one of the compounds in the virtually pure state the separation by distillation of the two original compounds by addition of a third compound capable of such behavior with one of them is called azeotropic distillation.

In azeotropic distillation, the third compound could be added to the original binary mixture prior to feeding into the column, or added separately into the column. The quantity of the solvent added is so selected that due to the different characteristics of mixing the third compound with the two original compounds, the composition-activity coefficient combination, called activity, of the third compound and one of the two original compounds are significantly higher than that of the third compound so that heteroazeotropic vapor mixture is formed in the top section of the column which is virtually free of the other compound of the original binary mixture. Upon condensation in the condenser, the heteroazeotropic mixture forms two separate liquids, one rich with the third compound while the other is rich with one of the compounds from the original binary mixture. After decantation, part or all of the third compound is refluxed into the column, the other liquid layer/stream being the separation product.

A mixture containing virtually all of the second compound of the original mixture and the remainder of the third compounds comes out as the bottoms stream of the column. As in extractive distillation, the third compound is so selected that this bottoms mixture can be separated.

Dichloromethane forms a tangential azeotrope with acetone having a boiling point of approximately 56.7° C. at 1 atmosphere pressure and having a composition of about 96% acetone at the pinch point which azeotrope cannot be separated into its components by simple distillation. However, addition of between about 2 and 50 moles of water to 1 mole of azeotrope achieves separation of dichloromethane from acetone and preferably the amount of water is between 5 and 20 moles.

Depending on the nature of the components the pressure in the distillation operation may or may not be critical. The vapor pressure of ketones and halogenated hydrocarbons increases relatively faster with temperature than the vapor pressure of water. When the boiling point of the preferred azeotrope of water with the organic components to be separated at the top of the column at atmospheric pressure is much higher than 100° C., it is desirable to perform the distillation under reduced pressure, e.g. 1/10th of an atmosphere, depending on the nature of the system and the economics involved. Among the advantages of reduced pressure operation are a further reduction of the heat input required to cover the heat losses and prevention of thermal decomposition of the organic materials.

The addition of water to a mixture to be separated can be either prior to distillation or as a separate distillation feed to the pot or the column. Also the condensed water can be either recovered, discarded or the same batch of water is continuously refluxed into the column thus reducing the need for fresh water feed.

Numerous types of equipment can be employed in the distillation process. A common type is a tray-type distillation column and the performance of other types of equipment is generally reduced to terms equivalent with the tray column for comparison. The distillation column can be a packed column with Raschig rings, pall or high efficiency packing ring, Berl saddles or other saddle-like packing, sultzer or flexipack packing or any grid type. As the selection of the nature or type of column internals, packing, trays or otherwise is immaterial to the distillation as long as sufficient equivalent of contact, or transfer units, is provided. The number of plates or equivalent thereof employed in the present invention should be at least 20 and preferably of at least 50 or its equivalent.

The halogenated compound is recovered as a separate liquid layer which is part of the overhead condensate, the other layer being water which is refluxed into the distillation column while the bottom stream consists of water and ketone with insignificant traces of halogenated compound. The water and ketone can then be separated by fractional distillation.

The separation as disclosed permits substantially complete recovery of practically pure halogenated compound for the preferred halogenated compounds of the present invention. Traces of ketone possibly remain in cases where the boiling point of the azeotrope between water and the halogenated compound is relatively high compared to that of the original azeotropic mixture of the two organic compounds.

The present invention can be practiced on a continuous basis as well as on a batch basis. The process of the present invention is useful in the production of organic materials employing solvents containing certain halogenated compounds and lower ketone.

EXAMPLE 1

Water was added into a liquid mixture containing 15.15 mole % dichloromethane and 84.85 mole % acetone thus diluting the mixture until the resulting mixture contained 12.83 mole % dichloromethane, 70.4 mole % of acetone and 17.13 mole % water. The ternary mixture was fed continuously into an Oldershaw column. The column contained a reboiler, fifty trays and a liquid splitting head condenser. The liquid mixture $F_1$ was fed into tray No. 30 counting from the reboiler. Also, a separate stream $F_2$ of distilled water was fed into tray No. 45, counting from the reboiler. At a reflux ratio of 4 to 1, the distillation was run continuously under atmospheric pressure for three hours and samples were taken and analyzed. The data in Table 1 show the recovery of all of the dichloromethane from the mixture. The overhead condensate contained 99.03% dichloromethane, 0.33% acetone and 0.63% water; all concentrations are in mole percent fractions. Redistillation of the bottoms stream under vacuum gave acetone of 99+ mole % purity.

EXAMPLE 2

A liquid mixture containing 15.88 mole % dichloromethane, 83.47 mole % acetone and 0.65 mole % water $F_1$ was continuously fed into the 30th tray, counted from the reboiler, of an Oldershaw column. A stream of distilled water $F_2$ was fed into the 40th tray, counting from the reboiler. The column was run for several hours at atmospheric pressure and at reflux ratio of 4 to 1 and later at reflux ratio of 10 to 1 and samples were taken and analyzed.

The data, also given in Table 1, demonstrate that dichloromethane of high purity 99.65% and even higher can be recovered from hard to separate and azeotropic mixtures with acetone.

TABLE 1

| | DATA FROM DISTILLATION EXPERIMENTS CONCENTRATION MOLE % | | | | | | | |
|---|---|---|---|---|---|---|---|---|
| | EXAMPLE 1 | | | | EXAMPLE 2 | | | |
| COMPOUND | $F_1$ | $F_2$ | OVHD | Bottoms | $F_1$ | $F_2$ | OVHD | Bottoms |
| Tray No. from Bottoms | 30 | 45 | 50 | 0 | 30 | 40 | 50 | |
| Acetone | 70.04 | | 0.33 | 28.62 | 83.47 | | 0.039 | 32.10 |
| Dichloromethane | 12.83 | | 99.03 | Nil | 15.88 | | 99.63 | Nil |
| Water | 17.13 | 100 | 0.63 | 71.38 | 0.65 | 100 | 0.33 | 67.90 |
| Tray Temp, °C. | 59.8 | 40 | 38.8 | 63.6 | 58 | 40 | 38 | 61.8 |
| P mm Hg | 760 | 760 | 760 | 810 | 757.1 | 757.1 | 757.1 | 807 |
| Rate, cc/hr | 350 | 80 | 53 | 420 | 265 | 140 | 25 | 380 |
| Reflux Ratio | | 4:1 | | | | 10:1 | | |

When azeotrope forming mixtures of lower ketones and certain halogenated compounds within the preview of the present invention are subjected to distillation in the presence of water in the manner above described and exemplified, similar results are obtained, that is to say, the azeotropes are effectively broken and the ketone and the halogenated compound can be effectively separated by distillation procedure.

Various changes may be made in the details and embodiments of this invention without departing from or sacrificing any of the advantages thereof.

We claim:

1. The method for separating mixtures of dialkyl ketones having three to five carbon atoms with halogenated compounds selected from the group consisting of
   (a) dihalogenated alkanes having two less carbon atoms than said ketone,
   (b) monohalogenated alkanes, straight chain or branched, having the same number of carbon atoms as said ketone and not more than four carbon atoms if the halogen is bromine,
   (c) monohalogenated dialkyl ethers having one carbon atom less than said ketone,
   (d) monohalogenated, mono-unsaturated alkenes having the same number of carbon atoms as said ketone, and
   (e) mixtures thereof which comprises subjecting said mixture of dialkyl ketones and halogenated compounds to distillation in the presence of water to obtain the halogenated compounds substantially in the overhead condensate and the dialkyl ketones substantially in the bottom streams.

2. The method as set forth in claim 1 wherein the mixture comprises acetone and 1,1-dichloromethane.

3. The method as set forth in claim 1 wherein the mixture comprises methylethylketone and 1,1-dichloroethane.

4. The method as set forth in claim 1 wherein the mixture comprises acetone and lower halogenated hydrocarbons selected from the group consisting of 1,1-dichloromethane, 3-chloropropane, 1-chloropropane, 2-chloro-2-methylpropane, 2-bromo-propane.

5. The method as set forth in claim 1 wherein the mixture comprises acetone and lower halogenated hydrocarbons selected from the group consisting of 1,1-dichloroethane, 3-chloropropane, 1-chloropropane, 2-chloro 2-methylpropane, 2-bromopropane, 2-chlorobutane, 1-chloro 2-methylpropane, 1-bromopropane, 3-bromopropane.

6. The method as set forth in claim 1 wherein the mixture is combined with water by adding the water before the distillation.

7. The method as set forth in claim 1 wherein the mixture is combined with water by adding water as a separate feed into a distillation system.

8. The method as set forth in claim 1 wherein the boiling points at atmospheric pressure of the dialkyl ketone and of the halogenated compound are below 100° C.

9. The method as set forth in claim 1 wherein the boiling points at atmospheric pressure of the dialkyl ketone and of the halogenated compound are below 80° C.

10. The method as set forth in claim 1 wherein the boiling points at atmospheric pressure of the dialkyl ketone and of the halogenated compound are below 70° C.

11. The method as set forth in claim 1 for separating mixtures of acetone and methylethylketone from chloromethyl methylether which comprises adding to such a mixture water; and separating the chloromethyl methylether from the ketone by distillation.

12. The method as set forth in claim 1 wherein the dialkyl ketone is a member of the group consisting of acetone and methyl ethyl ketone.

* * * * *